United States Patent [19]

Guley

[11] Patent Number: 4,681,765
[45] Date of Patent: Jul. 21, 1987

[54] RAPID RELEASING TRIAMTERENE CONTAINING GELATIN CAPSULE DOSAGE FORMS FOR ONCE DAILY ANTIHYPERTENSIVE USE

[75] Inventor: Paul C. Guley, Clinton, N.Y.

[73] Assignee: American Home Products Corporation, New York, N.Y.

[21] Appl. No.: 650,035

[22] Filed: Sep. 13, 1984

[51] Int. Cl.$^4$ .......................... A61K 9/22; A61K 9/40
[52] U.S. Cl. .................................... 424/456; 514/869; 514/960; 514/962; 514/778; 514/781; 424/455
[58] Field of Search ............... 514/869, 960, 962, 778, 514/781; 424/37, 156, 21

[56] References Cited

U.S. PATENT DOCUMENTS

| | | | |
|---|---|---|---|
| 2,883,327 | 4/1959 | Dale | 424/156 |
| 4,138,475 | 2/1979 | McAinsh et al. | 424/19 |
| 4,248,856 | 2/1981 | Guley et al. | 424/19 |
| 4,255,413 | 3/1981 | Rattie et al. | 424/37 |
| 4,444,769 | 4/1984 | Blume et al. | 424/20 |

*Primary Examiner*—Ronald W. Griffin
*Attorney, Agent, or Firm*—Walter Patton

[57] ABSTRACT

A gelatin capsule dosage form containing triamterene, 2,4,7-triamino-6-phenylpteridine, which results in rapid dissolution of the active ingredient. The dosage form comprises the pharmaceutical binder methylcellulose in combination with low doses of a surfactant or a carbonate salt as disintegrants.

11 Claims, No Drawings

RAPID RELEASING TRIAMTERENE CONTAINING GELATIN CAPSULE DOSAGE FORMS FOR ONCE DAILY ANTIHYPERTENSIVE USE

This invention relates to gelatin capsule dosage forms containing a combination of medicaments which includes triamterene as an active ingredient. Specifically, propranolol long acting spheroids and a hydrophobic hydrochlorothiazide-triamterene formulated powder were dual encapsulated in tandem into a hard gelatin capsule shell for once-a-day administration.

The utility of this capsule combination relates to the pharmacological action of each medicament. Propranolol hydrochloride, a known beta receptor blocker, has utility as an antihypertensive agent in that it reduces renin secretion by the kidney. Renin, via the renin-angiotensin system, stimulates aldosterone secretion that conserves sodium and which in turn conserves water to raise and maintain blood pressure.

Beta blockade of renin by propranolol hydrochloride is one pharmacological drug action to lower blood pressure.

Hydrochlorothiazide, a nonmercurial orally effective sulfonamide diuretic, potentiates the antihypertensive effect of propranolol hydrochloride by sodium, potassium, and water diuresis.

Triamterene, another nonmercurial orally effective diuretic, has additional utility in that it potentiates the action of other diurectics and in combination minimizes potassium diuresis. This is important due to the very narrow therapeutic index of the potassium ion and its relation to the sodium ion for normal biological activity.

Thus the utility of this triple combination dosage form lies in enhanced antihypertensive activity with potassium conservation in a convenient once-a-day capsule.

The formulation of a poorly soluble hydrophobic medicament such as triamterene in a gelatin capsule presents several problems. Due to the low solubility and hydrophobicity of triamterene, it is necessary to add excipients to lessen the hydrophobic character of the medicament. A disadvantage of formulation is that hydrophobic lubricants are necessary for machine encapsulation. These hydrophobic lubricants (e.g.: magnesium stearate) additionally interfere with triamterene release from the capsule shell.

The interference of triamterene release is caused by the dry coating of the inner gelatin capsule wall by the hydrophobic ingredients (e.g.: triamterene, hydrochlorothiazide, magnesium stearate, and talc) during encapsulation. On hydration in artifical gastric media, a hydrophobic gelatin interface forms that entraps the encapsulated dry powders and prevents rapid dispersion and dissolution of the active powder ingredients. Instead of obtaining a maximum surface area for the dissolving drug, which is a necessary requirement for a increased rate of solution, a minimum surface area is obtained. This results in erratic and slow rates of drug dissolution, dependent on the degree of hydrophobic dry coating within the gelatin capsule shell.

U.S. Pat. No. 4,255,413 discloses that the combination of a surfactant and carbonate or bicarbonate salt as diluents in a triamterene gelatin capsule dosage form overcomes the above stated problems.

A capsule dosage form containing propranolol hydrochloride film coated spheroids and a blended hydrochlorothiazide and triamterene powder was prepared that overcomes the hydrophobic gelatin interface problem that occurs on hydration. In addition, compression of these hydrophobic powders into one or two tablets further minimizes the hydrophobic gelatin barrier effect. This is very evident after high temperature dissolution comparison of dry powder and tablet encapsulated dosage forms.

Formulation of the blended hydrochlorothiazide and triamterene powder was completed using either a direct compression or mixed granulation method.

In the direct compression method, two disintegrants and a surfactant (sodium starch glycolate, calcium carbonate and sodium lauryl sulfate) were required to overcome the poor dissolution of triamterene. At least 17% by weight of the capsule contents consisted of disintegrants in order to increase the triamterene dissolution to an acceptable rate of not less than 60 percent in 30 minutes for in vitro capsule dissolution.

The mixed granulation method consists of granulating and drying the water stable formulation components. The water sensitive materials are sequentially added as a dry blend to the dried granulation. When the mixed granulation method was applied to this same formula, only 7 percent triamterene was released in 30 minutes (Formula I below).

Addition of 0.25 percent PEG 8000 increased the release rate of triamterene to more than 60 percent in 30 minutes, but this formulation was not stable under exaggerated high temperature stability conditions.

It has been unexpectedly discovered that in the presence of either a surfactant or calcium carbonate the addition of methylcellulose, a binder, increased the release of triamterene to more than 60 percent in 30 minutes. This formula displayed satisfactory stability after 5 weeks under exaggerated high temperature stability conditions.

It is therefore the object of this invention to provide a gelatin capsule dosage form of triamterene which provides a significantly better dispersion and faster dissolution of the medicament resulting in better absorption and bioavailability.

The compositions of this invention, as described above, are advantageously used in conjunction with beta blockers such as atenolol, nadolol, pindolol, timolol, metoprolol, alprenolol, labetalol, cetamolol, and propranolol hydrochloride. The preferred beta blocker is propranolol hydrochloride.

The compositions of this invention as described above are also advantageously used in conjunction with other non-pteridine diuretics, particularly with a thiazide diuretic. Exemplary of such thiazide diuretics are chlorothiazide, hydrochlorothiazide, flumethiazide, hydroflumethiazide, benzylhydroflumethiazide, trichloromethiazide or benzthiazide.

Advantageously the triamterene will be present in the capsule in an amount of from about 5 mg. to about 100 mg. and the hydrochlorothiazide of from about 2 mg. to about 250 mg and long acting propranolol hydrochloride from about 60 mg to 320 mg.

Following are triamterene in-vitro test results comparing the dissolution rate of capsule dosage forms containing long acting propranolol spheroids and quick release hydrochlorothiazide, triamterene with a variety of diluents.

TABLE I

| | Gram Quantities per 1000 Capsules | | | | | |
|---|---|---|---|---|---|---|
| | I | II | III | IV | V | VI |
| Propranolol L.A. Spheroid Strength (55% w/w) | 160.0 | 160.0 | 160.0 | 160.0 | 160 | 160 |
| Triamterene, USP | 50.0 | 50.0 | 50.0 | 50.0 | 50 | 50 |
| Hydrochlorothiazide, USP | 50.0 | 50.0 | 50.0 | 50.0 | 50 | 50 |
| Lactose, spray dried USP | 68.25 | 62.25 | 34.0 | 59.5 | 40 | 45.5 |
| Microcrystalline Cellulose, 101, NF | 27.0 | 27.0 | 27.0 | 27.0 | 27 | 27 |
| Sodium Starch Glycolate, NF | 27.0 | 27.0 | 27.0 | 27.0 | 27 | 27 |
| Calcium Carbonate, ppt | 16.0 | 16.0 | 20.0 | — | 20 | — |
| Sodium Lauryl Sulfate | 0.25 | 0.25 | — | 0.5 | — | 0.5 |
| Sodium Croscarmellose, Type A | — | — | 4.5 | 4.5 | 4.5 | 4.5 |
| Methylcellulose, 15 cps | — | 6.0 | 6.0 | 6.0 | 6.0 | 6.0 |
| Talc | 0.5 | 0.5 | 0.5 | 0.5 | 0.5 | 0.5 |
| Magnesium Stearate, USP | 1.0 | 1.0 | 1.0 | 1.0 | 1.0 | 1.0 |
| Theoretical Capsule Content Wt. "Powder only" | 240 mg. | 240 mg. | 220 mg. | 226 mg. | 226 mg. | 212 mg. |

0 Grey H.G.C. Formulae were machine encapsulated on a suitable capsule filler.

TABLE II

| | Percent Triamterene Dissolved | | | | |
|---|---|---|---|---|---|
| Formula | 7 minutes | 15 minutes | 30 minutes | 60 minutes | 90 minutes |
| I | 2 | 3 | 7 | 11 | 16 |
| II | 71 | 83 | 91 | 94 | 95 |
| III | 68 | 79 | 91 | 98 | 99 |
| IV | 28 | 58 | 87 | 94 | 95 |
| V | — | 45 | 68 | 87 | 95 |
| VI | — | 33 | 71 | 94 | 97 |

The above dissolution rate studies were performed in the USP Apparatus I (basket) in 900 ml. of artificial gastric fluid without enzyme at 37° C. and 100 RPM. This test is detailed under Dissolution, Apparatus 1, United States Pharmacopeia XX, National Formulary XV, page 959, released July 1, 1980.

Referring to the above Table I, it can be seen that Formula I and II containing long acting propranolol spheroids, and triamterene with hydrochlorothiazide both contain a surfactant, sodium lauryl sulfate, and calcium carbonate. It will be noted from Table II that in the case of Formula I, prepared by the mixed granulation method, only 7% of the triamterene dissolves over a 30 minute period.

When methylcellulose, a pharmaceutical binder, is added in Formula II, a very dramatic increase in dissolution of the triamterene results, i.e. from 7% to 91% in 30 minutes.

According to the present invention, it has been found that the presence of both a surfactant and calcium carbonate are not required to achieve a rapid release of triamterene provided that methylcellulose is present in the formula, to the extent of at least ¼% of the formula weight.

Reference to Formula III shows that in the absence of the surfactant, sodium lauryl sulfate, addition of 2.7% by weight of methylcellulose results in a rapid release of triamterene, i.e. 91% in 30 minutes. Reference to Formula IV shows that in the absence of the carbonate, calcium carbonate, addition of 2.7% by weight of methylcellulose results in a rapid increase of triamterene, i.e. 87% in 30 minutes.

In addition to calcium carbonate, it will be evident to one skilled in the pharmaceutical art that any nontoxic ammonium or alkali metal or amino acid metal, carbonate or bicarbonate salt may also be employed as an effervescent disintegrent in Formula II, III, and V of this invention. Exemplary of such carbonates or bicarbonates are magnesium carbonate, calcium carbonate, ammonium carbonate, sodium carbonate, sodium glycine carbonate, potassium carbonate, or sodium bicarbonate. The salts will be present from about 4% to about 40% by weight of the capsule formulation. Preferably the salts will be present at about 9% of the capsule formulation.

Exemplary of surfactants other than sodium lauryl sulfate which may be employed in Formula IV and VI of this invention are polysorbate derivatives such as polysorbate 80, cetyldimethylpyridinium chloride, and dioctyl sodium sulfosuccinate. The surfactant may be present in an amount of from about 0.05% to about 2.0% of the composition. Preferably the surfactant will be present at about 0.2% of the capsule formulation.

In addition, adjunctive disintegrant aids such as sodium croscarmellose, Type A, starch, calcium carboxy methyl cellulose, polyplasdone XL, alginic acid which are standard pharmaceutical excipients commonly used in capsule manufacturing may also be employed in the normal ranges commonly used preferably in the range of 2% to 15% by weight of the ingredients in the formula. The other ingredients are not an essential aspect of this invention, and those amounts can be varied.

Propranolol Hydrochloride L.A. Spheroid Preparation Procedure

The procedure for the preparation of propranolol hydrochloride long acting spheroids is set forth in U.S. Pat. No. 4,138,475, Feb. 6, 1979, which is herein incorporated by reference.

Triamterene and Hydrochlorothiazide Mixed Granulation Procedure

1. Triamterene, methylcellulose 15 cps, lactose, sodium starch glycolate, microcrystalline cellulose, talc and sodium lauryl sulfate, if desired, was added to a suitable mixer and dry mixed till blended.

2. Water was added in Step 1 and mixed till granulated.

3. The wet granulation was Fitzmilled using a #4 screen and dried to theoretical weight using a forced air oven (temperature not greater than 50° C. for drying) overnight.

4. The dried granulation was returned to a suitable mixer for blending and the water sensitive materials: the hydrochlorothiazide, calcium carbonate, sodium croscarmellose, and magnesium stearate was added to the same mixer and mixed till blended.

5. The total blended powder formula (Step #4) was passed through a Fitzmill at #2 screen and the Fitzmilled formula was blended in suitable mixer till uniform and than encapsulated.

In human bioavailability studies Formula III containing calcium carbonate, sodium starch glycolate, sodium croscarmellose type A, and methylcellulose but no sodium lauryl sulfate surfactant was found to be 93% bioavailable when compared to triamterene suspension reference standard. Statistically Formula III is bioequivalent to the suspension reference.

Formula IV containing sodium lauryl sulfate surfactant, sodium starch glycolate, sodium croscarmellose type A, and methylcellulose without calcium carbonate was found to be 74% bioavailable when compared to the triamterene suspension reference standard.

These relative triamterene bioavailability percents demonstrate the relative effectiveness of the carbonate Formula III and the surfactant Formula IV in providing a bioequivalent rapid releasing triamterene dosage form. It is clear from these results that "a rapid dissolution and dispersing amount of a combination of a surfactant and carbonate" are not solely necessary for bioequivalent triamterene absorption, in that the presence of carbonate and adjunctive excipients without a surfactant provides bioequivalent triamterene absorption when compared to the triamterene suspension reference standard. In contrast, the absence of a carbonate in the presence of a surfactant with the same other adjunctive excipients provides a lesser bioavailability that may be statistically bioequivalent for rapid releasing triamterene.

What is claimed is:

1. Method of producing triamterene and hydrochlorothiazide capsules by mixed granulation comprising the steps:
   (1) blending triamterene, methylcellulose, lactose, sodium starch glycolate, microcrystalline cellulose, and talc
   (2) adding water to the blend of step 1 and mixing till granulated
   (3) milling and drying the wet granulation of step 2
   (4) blending the dried granulation of step 3 with hydrochlorothiazide, calcium carbonate, sodium croscarmellose and magnesium stearate and
   (5) milling, and blending the blend of step 4 and encapsulating.

2. Method of treating hypertension by the administration of a gelatin capsule dosage unit comprising triamterene, propranolol long acting spheres, hydrochlorothiazide, and
   (a) a rapid dispersing amount of a calcium, magnesium, ammonium, aminoacid, or alkali metal nontoxic carbonate or bicarbonate salt in the presence of adjunctive disintegrant aids selected from the group consisting of sodium starch glycolate, sodium croscarmellose and methylcellulose in the absence of a surfactant.

3. An improved rapid dispersing gelatin capsule dosage unit comprising triamterene in the presence of adjunctive disintegrant aids selected from the group consisting of sodium starch glycolate, sodium croscarmellose, and methylcellulose, wherein the improvement comprises the addition of a rapid dispersing amount of a calcium, magnesium, ammonium, aminoacid, or alkali metal nontoxic carbonate or bicarbonate salt in the absence of a surfactant.

4. The gelatin capsule of claim 3 in which the carbonate salt is calcium carbonate.

5. The gelatin capsule of claim 4 in which the triamterene is present in an amount of from 5 mg. to 100 mg., the carbonate salt is present in an amount of from about 4% to about 40% and the adjunctive disintegrant aids are present in an amount of from about 2% to about 15% by weight of the ingredients in the formula.

6. An improved rapid dispersing gelatin capsule dosage unit comprising triamterene and hydrochlorothiazide in the presence of adjunctive disintegrant aids selected from the group consisting of sodium starch glycolate, sodium croscarmellose, and methylcellulose, wherein the improvement comprises the addition of a rapid dispersing amount of a calcium, magnesium, ammonium, aminoacid, or alkali metal nontoxic carbonate or bicarbonate salt in the absence of a surfactant.

7. The gelatin capsule of claim 6 in which the carbonate salt is calcium carbonate.

8. The gelatin capsule of claim 6 in which the triamterene is present in an amount of from 5 mg. to 100 mg. and the hydrochlorothiazide is present in an amount of from 2 mg. to 250 mg., the carbonate salt is present in an amount of from about 4% to about 40% and the adjunctive ingredient aids are present in an amount of from about 2% to about 15% by weight of the ingredients in the formula.

9. An improved rapid dispersing gelatin capsule dosage unit comprising triamterene, hydrochlorothiazide and propranolol hydrochloride in the presence of adjunctive disintegrant aids selected from the group consisting of sodium starch glycolate, sodium croscarmellose, and methylcellulose, wherein the improvement comprises the addition of a rapid dispersing amount of a calcium, magnesium, ammonium, aminoacid, or alkali metal nontoxic carbonate or bicarbonate salt in the absence of a surfactant.

10. The gelatin capsule of claim 9 in which the carbonate salt is calcium carbonate.

11. The gelatin capsule of claim 9 in which the triamterene is present in an amount of from about 5 mg. to about 100 mg. and the hydrochlorothiazide is present in an amount of from about 2 mg. to about 250 mg., and the propranolol long acting spheroids are present in an amount from 60 mg. to 320 mg., the carbonate salt is present in an amount of from about 4% to about 40% and the adjunctive disintegrant aids are present in an amount of from about 2% to about 15% by weight of the ingredients in the formula.

* * * * *